US012636171B2

(12) United States Patent
Ye et al.

(10) Patent No.: US 12,636,171 B2
(45) Date of Patent: May 26, 2026

(54) FENESTRATED DUODENAL STENT

(71) Applicant: TAIZHOU ENZE MEDICAL CENTER (GROUP), Taizhou (CN)

(72) Inventors: Liping Ye, Taizhou (CN); Shenkang Zhou, Taizhou (CN); Xinli Mao, Taizhou (CN); Shaowei Li, Taizhou (CN); Jianyu Wei, Nanjing (CN)

(73) Assignee: TAIZHOU ENZE MEDICAL CENTER (GROUP), Taizhou (CN)

( * ) Notice: Subject to any disclaimer, the term of this patent is extended or adjusted under 35 U.S.C. 154(b) by 506 days.

(21) Appl. No.: 18/221,906

(22) Filed: Jul. 14, 2023

(65) Prior Publication Data

US 2024/0164918 A1 May 23, 2024

(30) Foreign Application Priority Data

Nov. 22, 2022 (CN) .......................... 202211467982.6

(51) Int. Cl.
*A61F 2/90* (2013.01)
*A61F 2/04* (2013.01)

(52) U.S. Cl.
CPC .......... *A61F 2/90* (2013.01); *A61F 2002/045* (2013.01); *A61F 2230/0069* (2013.01); *A61F 2230/0071* (2013.01); *A61F 2230/0093* (2013.01)

(58) Field of Classification Search
CPC .................. A61F 2/90; A61F 2002/045; A61F 2230/0069; A61F 2230/0071; A61F 2230/0093; A61F 2/04
See application file for complete search history.

(56) References Cited

U.S. PATENT DOCUMENTS

| | | | | |
|---|---|---|---|---|
| 4,230,123 A | * | 10/1980 | Hawkins, Jr. ...... | A61B 10/0283 |
| | | | | 604/165.02 |
| 5,174,290 A | * | 12/1992 | Fiddian-Green ..... | A61B 5/1473 |
| | | | | 600/573 |
| 2003/0065377 A1 | * | 4/2003 | Davila ................... | A61L 31/10 |
| | | | | 623/1.42 |

(Continued)

FOREIGN PATENT DOCUMENTS

| | | |
|---|---|---|
| CN | 102123683 A | 7/2011 |
| CN | 106999272 A | 8/2017 |

(Continued)

*Primary Examiner* — Suzette J Gherbi
(74) *Attorney, Agent, or Firm* — Bayramoglu Law Offices LLC

(57) ABSTRACT

A fenestrated duodenal stent includes a stent body enclosed by a meshed sidewall. The stent body is open at two ends and hollow inside. The stent body includes a proximal support segment, a distal support segment, and an opening segment connected between the proximal and distal support segments. The proximal support segment is divided into a front section, a middle section and a rear section that are connected sequentially and coaxially. The front section is of an umbrella shape, and an opening of the umbrella shape faces the middle section. The middle section is of a cylindrical shape, and a diameter of the cylindrical shape is less than a diameter of the opening segment. The rear section is spherical or hemispherical, and a maximum diameter of the rear section is greater than the diameter of the opening segment but not greater than a maximum diameter of the umbrella shape.

9 Claims, 3 Drawing Sheets

(56)  References Cited

U.S. PATENT DOCUMENTS

| | | | |
|---|---|---|---|
| 2005/0043817 A1* | 2/2005 | McKenna | A61F 5/0076 |
| | | | 623/23.65 |
| 2005/0059990 A1* | 3/2005 | Ayala | A61M 25/0662 |
| | | | 606/192 |
| 2007/0100437 A1* | 5/2007 | Welborn | A61F 2/915 |
| | | | 623/1.44 |
| 2008/0051911 A1* | 2/2008 | Rucker | A61F 2/04 |
| | | | 623/23.7 |
| 2009/0093875 A1* | 4/2009 | Stalker | A61L 31/16 |
| | | | 623/1.42 |
| 2009/0149947 A1* | 6/2009 | Frohwitter | A61L 27/54 |
| | | | 623/1.42 |
| 2012/0095384 A1* | 4/2012 | Babkes | A61F 5/0033 |
| | | | 604/9 |
| 2013/0138219 A1* | 5/2013 | Toomey | A61F 2/07 |
| | | | 623/23.7 |
| 2013/0289466 A1* | 10/2013 | Babkes | A61F 5/0079 |
| | | | 604/8 |
| 2014/0236064 A1* | 8/2014 | Binmoeller | A61F 5/0076 |
| | | | 604/8 |
| 2015/0283308 A1* | 10/2015 | Chutka | A61L 31/16 |
| | | | 623/23.7 |
| 2017/0056164 A1* | 3/2017 | Wang | A61F 2/844 |
| 2022/0265417 A1* | 8/2022 | Baranowski | A61F 2/07 |
| 2022/0313461 A1* | 10/2022 | Hasegawa | A61F 2/90 |
| 2024/0164920 A1* | 5/2024 | Folan | A61F 2/07 |
| 2024/0252305 A1* | 8/2024 | Folan | A61F 2/04 |
| 2026/0013979 A1* | 1/2026 | Hasegawa | A61F 2/04 |

FOREIGN PATENT DOCUMENTS

| | | | |
|---|---|---|---|
| CN | 108635092 A | | 10/2018 |
| CN | 109195529 A | | 1/2019 |
| CN | 114569302 A | | 6/2022 |
| CN | 115813603 A | | 3/2023 |
| JP | 2021153895 A | * | 10/2021 |
| WO | 2020195841 A1 | | 10/2020 |

* cited by examiner

FENESTRATED DUODENAL STENT

CROSS REFERENCE TO THE RELATED APPLICATIONS

This application is based upon and claims priority to Chinese Patent Application No. 202211467982.6, filed on Nov. 22, 2022, the entire contents of which are incorporated herein by reference.

TECHNICAL HELD

The present disclosure belongs to the technical field of interventional medical devices, and particularly relates to a fenestrated duodenal stent.

BACKGROUND

At present, the self expandable metal stent (SEMS) has been widely applied to treating Obstructive diseases of the digestive tract. The SEMS is often applied to various regions of the digestive tract, including an esophageal stent, a duodenal stent, a colonic stent, a biliary stent and the like. The stent specifically includes a covered stent and an uncovered stent.

The uncovered stent can effectively prevent displacement through mucosal hyperplasia of the digestive tract, but is hard to be taken out and prone to causing damage to tissues and organs.

The covered stent can be taken out conveniently. However, poor positioning can lead to displacement after implantation in the digestive tract. Moreover, because the covered stent is completely enclosed, a failure in fistula occlusion can occur. For example, a duodenal covered stent in occlusion of an intestinal fistula can further occlude a duodenal papilla. In this example, the orifice of the papilla is oppressed for a long time, affecting discharge of bile and pancreatic fluid. The discharged bile and pancreatic fluid, also positioned outside the covered stent, can flow into the fistula along the surface of the stent, and thus affect the fistula occluding effect or cause a fistula occluding failure.

SUMMARY

In view of the problem in the background, an objective of the present disclosure is to provide a fenestrated duodenal stent.

To achieve the above objective, the present disclosure provides the following technical solutions:

A fenestrated duodenal stent includes a stent body enclosed by a meshed sidewall, where the stent body is open at two ends and hollow inside and the stent body includes a proximal support segment, a distal support segment, and an opening segment connected between the proximal support segment and the distal support segment;

the proximal support segment is divided into a front section, a middle section and a rear section that are connected sequentially and coaxially;

the front section is of an umbrella shape, and an opening of the umbrella shape faces the middle section;

the middle section is of a cylindrical shape, and a diameter of the cylindrical shape is less than a diameter of the opening segment; and the rear section is of a spherical shape or a hemispherical shape, and a maximum diameter of the rear section is greater than the diameter of the opening segment but not greater than a maximum diameter of the umbrella shape.

Preferably, a membrane covers a surface of the stent body, and an uncovered window for allowing a liquid to pass through and flow to a port of the proximal support segment via a hollow region in the stent body is formed in a local region of a sidewall of the opening segment.

Specifically in response to use: the front section of the proximal support segment is positioned in a stomach, and abuts against an inner wall of the stomach; the middle section of the proximal support segment is positioned in a pylorus; the rear section of the proximal support segment is positioned on a duodenal bulb, and abuts against a duodenal wall of the duodenal bulb; and the uncovered window is positioned outside a duodenal papilla, and an opening edge of the uncovered window abuts against the duodenal wall around the duodenal papilla.

Compared with the prior art, the present disclosure has the following beneficial effects:

(1) The proximal support segment of the stent body is divided into a front section, a middle section and a rear section that are connected sequentially and coaxially. The front section is of an umbrella shape, and can stably abut against a stomach in use. The rear section is of a spherical shape or a hemispherical shape, and can stably abut against a duodenal bulb in use. Therefore, the whole stent body can be firmly clamped at the pylorus, thereby preventing displacement of the stent, and reducing damage of the stent on tissues and organs.

(2) The opening segment is provided outside the duodenal papilla. An uncovered window is formed in the opening segment. An opening edge of the uncovered window in use abuts against the duodenal wall around the duodenal papilla. Therefore, bile and pancreatic fluid discharged by the papilla can directly flow into the stent, and flow back to the stomach through the stent and the port of the proximal support segment. On one hand, the bile and pancreatic fluid do not flow into the fistula to realize effective occlusion on the fistula. On the other hand, the backflow of the bile and pancreatic fluid can promote digestion in the stomach.

In the figures: 100: stent body, 200: membrane, and 300: skirt; and

11: proximal support segment, 12: distal support segment, 13: opening segment, and 14: uncovered window.

DETAILED DESCRIPTION OF THE EMBODIMENTS

The technical solutions in the embodiments of the present disclosure are clearly and completely described below with reference to the accompanying drawings in the embodiments of the present disclosure. Apparently, the described embodiments are merely a part rather than all of the embodiments of the present disclosure. All other embodiments obtained by a person of ordinary skill in the art based on the embodiments of the present disclosure without creative efforts shall fall within the protection scope of the present disclosure.

Figure 1:
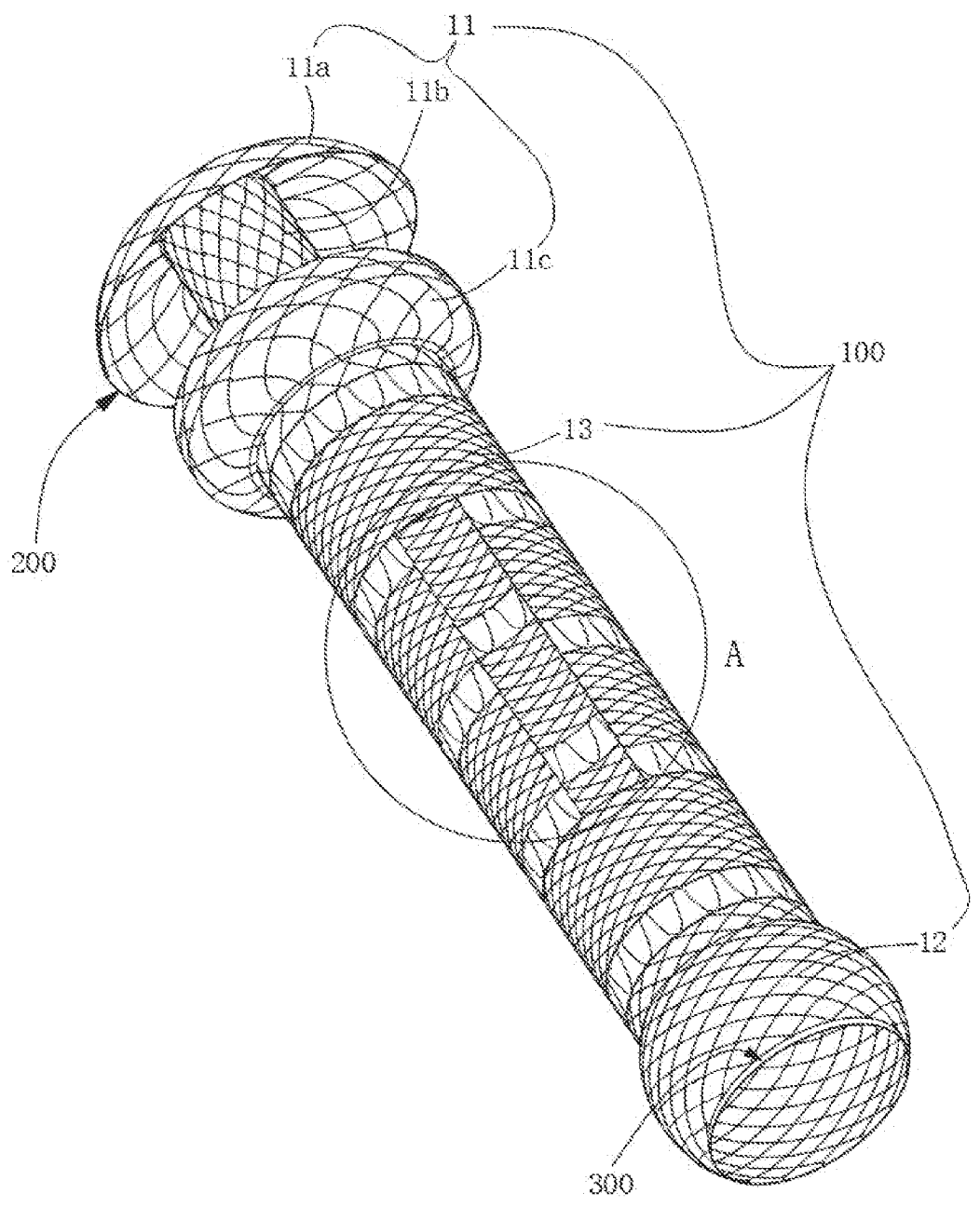
FIG. 1 is a perspective view of a fenestrated duodenal stent according to the present disclosure.

As shown in FIG. 1, a fenestrated duodenal stent in the embodiment includes stent body 100 (which is preferably made of a nickel-titanium memory alloy) enclosed by a meshed sidewall. The stent body 100 is open at two ends and hollow inside.

Membrane 200 covers a surface of the stent body 100. The membrane 200 extends toward an outer side of each of the two ends of the stent body 100 to form skirt 300. The stent body 100 specifically includes proximal support segment 11, distal support segment 12, and opening segment 13 connected between the proximal support segment 11 and the distal support segment 12.

Specifically:

The stent body 100 has a total axial length of 140 mm to 142 mm, preferably 141 mm.

The proximal support segment 11 preferably has an axial length of 32 mm. The proximal support segment 11 is divided into front section 11a, middle section 11b, and rear section 11c that are connected sequentially and coaxially. The front section 11a is of an umbrella shape, and, has an axial length of 9.5 m, a minimum diameter of 14 mm, and a maximum diameter of 40 mm. An opening of the umbrella shape faces the middle section 11b. The middle section 11b is of a cylindrical shape. One end of the middle section 11b is connected to the front section 11a. Correspondingly, the middle section 11b preferably has a diameter of 14 mm. The rear section 11c is of a spherical shape or a hemispherical shape, and has an axial length of 12 mm, and a maximum diameter of 36 mm.

The distal support segment 12 is of a spherical shape or a hemispherical shape. The distal support segment 12 has an axial length of 17 ruin, a minimum diameter of 24 mm, and a maximum diameter of 30 mm.

Figure 2:
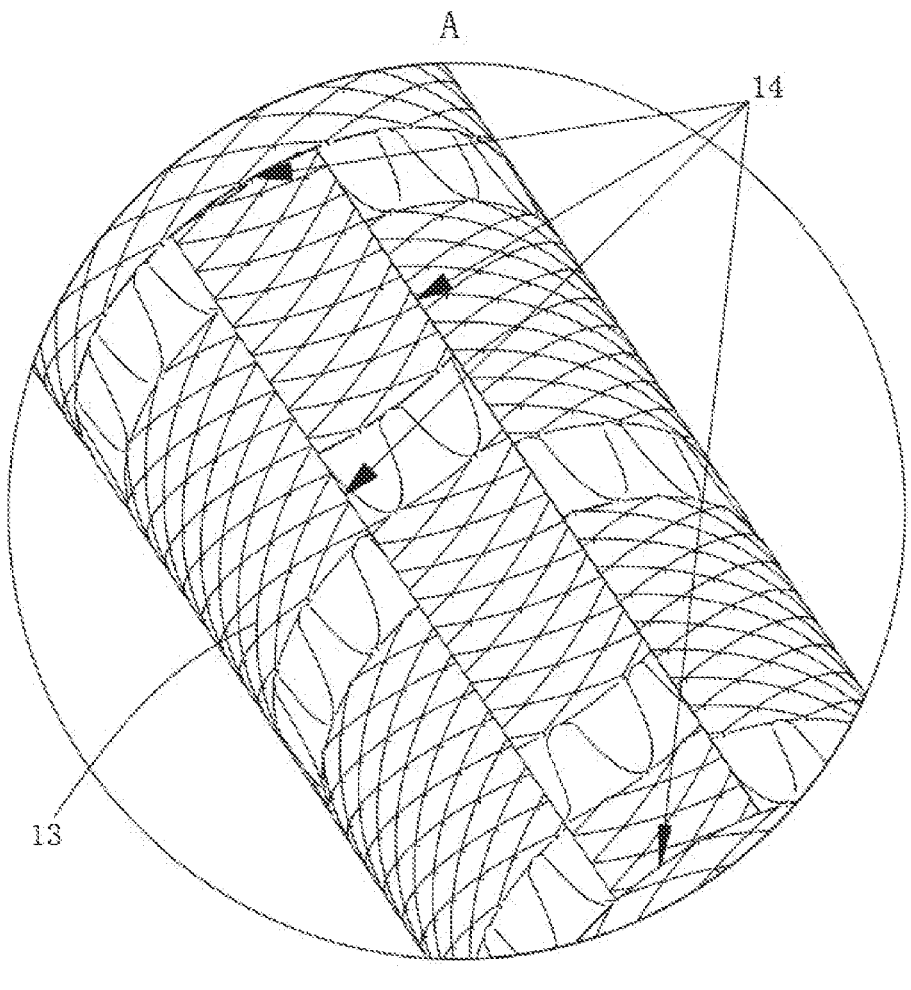
FIG. 2 is an enlarged view of a position A shown in FIG. 1.
Figure 3:
FIG. 3 is a plane view of a fenestrated duodenal stent according to the present disclosure.

The opening segment 13 is of a cylindrical shape, One end of the opening segment 13 is connected to the distal support segment 12. Correspondingly, the opening segment 13 preferably has a diameter of 24 mm. In addition, referring to FIG. 2, uncovered window 14 for allowing a liquid to pass through and flow to a port of the proximal support segment via a hollow region in the stent body 100 is formed in a local region of a sidewall of the opening segment 13. Preferably, the uncovered window 14 has a size of 8 mm*45 mm (an opening edge of the uncovered window 14 refers to four edge lines indicated by arrows in FIG. 2).

Specifically, in response to use of the fenestrated duodenal stent:

A) The fenestrated duodenal stent is sleeved on an enteroscope. Three 30-mm snares are respectively used to control contraction of the proximal support segment 11, the distal support segment 12, and the opening segment 13.

B) The enteroscope enters a digestive tract together with the fenestrated duodenal stent and the three snares.

The front section 11a of the proximal support segment 11 is positioned in a stomach, and, abuts against an inner wall of the stomach.

The middle section 11b of the proximal support segment 11 is positioned in a pylorus.

The rear section 11c of the proximal support segment 11 is positioned on a duodenal bulb, and abuts against a duodenal wall of the duodenal bulb.

The uncovered window 14 is positioned outside a duodenal papilla, and the opening edge of the uncovered window 14 abuts against the duodenal wall around the duodenal papilla.

C) The three snares are loosened sequentially, and the fenestrated duodenal stent is released.

D) The fenestrated duodenal stent is fine adjusted with foreign body forceps.

E) The enteroscope is drawn back, thereby realizing fistula occlusion of the fenestrated duodenal stent.

In conclusion, with the front section 11a, the middle section 11b and the rear section 11c of the proximal support segment 11, the fenestrated duodenal stent can be firmly clamped at the pylorus without displacement. With the uncovered window 14, the bile and pancreatic fluid discharged by the duodenal papilla can directly flow into the stent, and then flows back to the stomach through the hollow region in the stent body 100 and the port of the proximal support segment 11, thereby realizing effective occlusion of the fistula. Moreover, the backflow of the bile and pancreatic fluid can further promote digestion of the stomach.

Although embodiments of the present disclosure have been illustrated and described, it can be understood by a person of ordinary skill in the art that various changes, modifications, replacements, and variations may be made to the embodiments without departing from the principle and spirit of the present disclosure, and the scope of the present disclosure is subject to the appended claims and equivalents thereof.

What is claimed is:

1. A fenestrated duodenal stent, comprising a stent body enclosed by a meshed sidewall, wherein the stent body is open at two ends and hollow inside;

the stent body comprises a proximal support segment, a distal support segment, and an opening segment connected between the proximal support segment and the distal support segment;

a membrane covers a surface of the stent body, and an uncovered window for allowing a liquid to pass through and flow to a port of the proximal support segment via a hollow region in the stent body is formed in a local region of a sidewall of the opening segment; and wherein the distal support segment is of a spherical shape or a hemispherical shape, and a maximum diameter of the distal support segment is greater than a diameter of the opening segment but less than or equal to a maximum diameter of a rear section of the proximal support segment.

2. The fenestrated duodenal stent according to claim 1, wherein in response to a use state of the stent body:

the uncovered window is positioned outside a duodenal papilla, and an opening edge of the uncovered window abuts against a duodenal wall around the duodenal papilla.

3. The fenestrated duodenal stent according to claim 1, wherein the membrane extends toward an outer side of each of the two ends of the stent body to form a skirt.

4. The fenestrated duodenal stent according to claim 1, wherein the proximal support segment is divided into a front section, a middle section and a rear section, wherein the front section, the middle section and the rear section are connected sequentially and coaxially;

the front section is of an umbrella shape, and an opening of the umbrella shape faces the middle section;

the middle section is of a cylindrical shape, and a diameter of the cylindrical shape is less than a diameter of the opening segment; and the rear section is of a spherical shape or a hemispherical shape, and a maximum diameter of the rear section is greater than the diameter of the opening segment but less than or equal to a maximum diameter of the umbrella shape.

5. The fenestrated duodenal stent according to claim 4, wherein in response to a use state of the stent body:

the front section of the proximal support segment is positioned in a stomach, and abuts against an inner wall of the stomach;

the middle section of the proximal support segment is positioned in a pylorus; and the rear section of the proximal support segment is positioned on a duodenal bulb, and abuts against a duodenal wall of the duodenal bulb.

6. The fenestrated duodenal stent according to claim 1, wherein the stent body has a total axial length of 140 mm to 142 mm.

7. The fenestrated duodenal stent according to claim 6, wherein the proximal support segment has an axial length of 30 mm to 32 mm; and the distal support segment has an axial length of 16 mm to 18 mm, a minimum diameter of 24 mm, and a maximum diameter of 30 mm.

8. The fenestrated duodenal stent according to claim 7, wherein a front section of the proximal support segment has an axial length of 9 mm to 9.5 mm, a minimum diameter of 14 mm, and a maximum diameter of 40 mm.

9. The fenestrated duodenal stent according to claim 7, wherein a rear section of the proximal support segment has an axial length of 11 mm to 13 mm, and a maximum diameter of 36 mm.

\* \* \* \* \*